US012767977B2

(12) United States Patent
Porter et al.

(10) Patent No.: US 12,767,977 B2
(45) Date of Patent: Oct. 20, 2026

(54) METHODS AND KITS FOR THE DETECTION OF SARS-CoV-2

(71) Applicant: THE TRANSLATIONAL GENOMICS RESEARCH INSTITUTE, Phoenix, AZ (US)

(72) Inventors: William Tanner Porter, Flagstaff, AZ (US); Erin Kelley, Flagstaff, AZ (US); Jolene Bowers, Flagstaff, AZ (US); David Engelthaler, Flagstaff, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 888 days.

(21) Appl. No.: 17/937,117

(22) Filed: Sep. 30, 2022

(65) Prior Publication Data

US 2023/0094433 A1 Mar. 30, 2023

Related U.S. Application Data

(60) Provisional application No. 63/251,030, filed on Sep. 30, 2021.

(51) Int. Cl.
*C12Q 1/68* (2018.01)
*C12Q 1/6851* (2018.01)
*C12Q 1/6853* (2018.01)
*C12Q 1/686* (2018.01)

(52) U.S. Cl.
CPC ......... *C12Q 1/6853* (2013.01); *C12Q 1/6851* (2013.01); *C12Q 1/686* (2013.01)

(58) Field of Classification Search
None
See application file for complete search history.

(56) References Cited

U.S. PATENT DOCUMENTS

2019/0002958 A1* 1/2019 Cabannes ............ C12Q 1/6806

OTHER PUBLICATIONS

Lowe, T et al. A computer program for selection of oligonucleotide primers for polymerase cahin reaction. Nucleic Acids Research, vol. 18(7), p. 1757-1761, (1990).*
Petrillo et al. A novel multiplex qRT-PCR assay to detect SARS-CoV-2 infection: high sensitivity and increased testing capacity. Microroganisms, vol. 8, 1064, p. 1-10, (2020).*
Piralla, A., et al. Cellular DNA quantitation in respiratory samples for the normalization of viral load: a real need ?. Journal of Clinical Virology, vol. 107, p. 6-10, (2018).*
Long, S., et al. Maximizing viral detection with SIV droplet digital PCR (ddPCR) assays. PLOS One, vol. 15(5): e0233085, p. 1-20, (2020).*
Beigel, J. H. et al. Remdesivir for the Treatment of Covid-19—Final Report. N. Engl. J. Med. 383, 1813-1826 (2020).
Caillard, S., Benotmane, I., Gautier Vargas, G., Perrin, P. & Fafi-Kremer, S. SARS-CoV-2 viral dynamics in immunocompromised patients. Am. J. Transplant. (2020) doi:10.1111/ajt.16353.
Cao, B. et al. A trial of lopinavir-ritonavir in adults hospitalized with severe covid-19. N. Engl. J. Med. 382, 1787-1799 (2020).
Dahdouh, E., Lázaro-Perona, F., Romero-Gómez, M. P., Mingorance, J. & García-Rodriguez, J. Ct values from SARS-CoV-2 diagnostic PCR assays should not be used as direct estimates of viral load. J. Infect. 2020-2022 (2020) doi:10.1016/j.jinf.2020.10.017.
Gottlieb, R. L. et al. Effect of Bamlanivimab as Monotherapy or in Combination with Etesevimab on Viral Load in Patients with Mild to Moderate COVID-19: A Randomized Clinical Trial. JAMA—J. Am. Med. Assoc. 325(7): 632-644.
Han, M. S., Byun, J. H., Cho, Y. & Rim, J. H. RT-PCR for SARS-CoV-2: quantitative versus qualitative. Lancet Infect. Dis. 21, 165 (2021).
Jacob, F. et al. Careful Selection of Reference Genes Is Required for Reliable Performance of RT-qPCR in Human Normal and Cancer Cell Lines. PLoS One 8, (2013).
Kozera, B. & Rapacz, M. Reference genes in real-time PCR. J. Appl. Genet. 54, 391-406 (2013).
Liu, Y et al. Viral dynamics in mild and severe cases of COVID-19. Lancet Infect. Dis. 20, 656-657 (2020).
Pan, Y., Zhang, D., Yang, P., Poon, L. L. M. & Wang, Q. Viral load of SARS-CoV-2 in clinical samples. Lancet Infect. Dis. 20, 411-412 (2020).
Piubelli, C et al. Overall decrease in SARS-CoV-2 viral load and reduction in clinical burden: the experience of a hospital in northern Italy. Clin. Microbiol. Infect. 27, 131.e1-131.e3 (2021).
Schmittgen, T. D. & Livak, K. J. Analyzing real-time PCR data by the comparative CT method. Nat. Protoc. 3, 1101-1108 (2008).
Shen, C. et al. Treatment of 5 Critically Ill Patients with COVID-19 with Convalescent Plasma. JAMA—J. Am. Med. Assoc. 323, 1582-1589 (2020).
The RECOVERY Collaborative Group. Dexamethasone in Hospitalized Patients with Covid-19. N. Engl. J. Med. 384, 693-704 (2021).
U.S. Food and Drug Administration. Emergency Use Authorization. https://www.fda.gov/emergency-preparedness-and-response/mcm-legal-regulatory-and-policy-framework/emergency-use-authorization (2021).
Zhou, R. et al. Viral dynamics in asymptomatic patients with COVID-19. Int. J. Infect. Dis. 96, 288-290 (2020).
Holland, et al., Proc. Natl. Adad. Sci, USA 88:7276-7280, 1991.
Heid, et al, Genome Research 6:986-994, 1996.

* cited by examiner

*Primary Examiner* — Suryaprabha Chunduru
(74) *Attorney, Agent, or Firm* — FULLER IP LAW LLC; Rodney J. Fuller

(57) ABSTRACT

Methods, kits, and oligonucleotides used in the detection of the coronavirus strain, severe acute respiratory syndrome coronavirus 2 (SARS-CoV-2), are disclosed. In some aspects, the oligonucleotides are primers or probes used in the described methods or kits. The oligonucleotide consists of 40 or less nucleotides and has a nucleotide sequence that consists essentially of, or is a variant of, the nucleotide sequence of: SEQ ID NO:7, SEQ ID NO:8, SEQ ID NO:9, or SEQ ID NO:10.

8 Claims, 7 Drawing Sheets

Specification includes a Sequence Listing.

| Sample | Control Concentration (copies/ul) | 2020.06.10 | 2020.06.16 | 2020.06.18 | 2020.06.20 | 2020.06.27 | 2021.01.22 | 2021.03.16 | Aggregated Data |
|---|---|---|---|---|---|---|---|---|---|
| SS1 | 1.31E+09 | 6.07 (0.02, 1.38%) [4/4] | 6.65 (0.02, 1.38%) [2/2] | 5.94 (0.17, 11.74%) [2/2] | 6.26 (0.06, 4.13%) [2/2] | 6.22 (0.02, 1.38%) [2/2] | NA | NA | 6.2 (0.24, 16.63%) [12/12] |
| SS3 | 1.31E+07 | 12.53 (0.13, 8.96%) [4/4] | 11.91 (0.1, 6.89%) [2/2] | 12 (0.03, 2.06%) [2/2] | 12.03 (0.34, 23.72%) [2/2] | 11.85 (0.09, 6.2%) [2/2] | 11.74 (0.06, 4.13%) [4/4] | 11.1 (0.15, 10.35%) [2/2] | 11.94 (0.43, 30.25%) [18/18] |
| SS5 | 1.31E+05 | 19.61 (0.17, 11.74%) [4/4] | 18.65 (0.3, 20.87%) [2/2] | 18.88 (0.19, 13.13%) [2/2] | 19.01 (0.05, 3.44%) [2/2] | 18.91 (0.03, 2.06%) [2/2] | 18.39 (0.25, 17.33%) [2/2] | 17.96 (0.09, 6.2%) [2/2] | 18.88 (0.56, 40.01%) [16/16] |
| SS7 | 1.31E+03 | 26.34 (0.22, 15.23%) [4/4] | 25.52 (0.18, 12.43%) [2/2] | 25.82 (0.03, 2.06%) [2/2] | 25.89 (0.09, 6.2%) [2/2] | 25.9 (0.04, 2.75%) [2/2] | 25.11 (0.01, 0.69%) [2/2] | 25.78 (0.2, 13.83%) [2/2] | 25.84 (0.41, 28.78%) [16/16] |
| SS9 | 6.53E+02 | 27.14 (0.06, 4.13%) [4/4] | 27.05 (0.25, 17.33%) [2/2] | 26.98 (0.11, 7.58%) [2/2] | 26.88 (0.03, 2.06%) [2/2] | 26.81 (0.06, 4.13%) [2/2] | 26.73 (0.14, 9.66%) [2/2] | 26.35 (0.43, 30.25%) [2/2] | 26.88 (0.29, 20.16%) [16/16] |
| SS10 | 3.27E+02 | 28.02 (0.04, 2.75%) [4/4] | 27.82 (0.08, 5.51%) [2/2] | 27.97 (0.28, 19.45%) [2/2] | 27.87 (0.07, 4.82%) [2/2] | 27.8 (0.04, 2.75%) [2/2] | 27.81 (0.23, 15.93%) [2/2] | 27.03 (1.17, 95.51%) [2/2] | 27.79 (0.44, 30.99%) [16/16] |
| SS11 | 1.63E+02 | 29.04 (0.05, 3.44%) [4/4] | 29.09 (0.13, 8.96%) [2/2] | 28.99 (0.1, 6.89%) [2/2] | 29.06 (0.13, 8.96%) [2/2] | 29.05 (0.22, 15.23%) [2/2] | 28.75 (0.06, 4.13%) [2/2] | 29.93 (0.53, 37.72%) [7/7] | 29.31 (0.55, 39.24%) [21/21] |
| SS12 | 8.17E+01 | 30.31 (0.11, 7.58%) [4/4] | 30.15 (0.05, 3.44%) [2/2] | 30.07 (0.22, 15.23%) [2/2] | 30.07 (0.13, 8.96%) [2/2] | 29.97 (0.12, 8.27%) [2/2] | 29.76 (0.12, 8.27%) [2/2] | 30.67 (0.76, 56.09%) [2/2] | 30.16 (0.34, 23.72%) [16/16] |
| SS13 | 4.08E+01 | 31.58 (0.13, 8.96%) [4/4] | 31.1 (0.06, 4.13%) [2/2] | 31.17 (0.08, 5.51%) [2/2] | 31.14 (0.24, 16.63%) [2/2] | 31.12 (0.29, 20.16%) [2/2] | 30.87 (0.22, 15.23%) [2/2] | 31.82 (0.13, 8.96%) [2/2] | 31.3 (0.34, 23.72%) [16/16] |
| SS14 | 2.04E+01 | 32.46 (0.33, 23%) [4/4] | 32.03 (0.27, 18.74%) [2/2] | 31.81 (0.05, 3.44%) [2/2] | 32.3 (0.23, 15.93%) [2/2] | 32.39 (0.04, 2.75%) [2/2] | 31.91 (1.49, 136.43%) [4/4] | 32.94 (0.21, 14.53%) [2/2] | 32.24 (0.74, 54.41%) [18/18] |
| SS15 | 1.02E+01 | 33.57 (0.58, 41.56%) [4/4] | 33.12 (0.48, 33.95%) [2/2] | 32.8 (0.15, 10.35%) [2/2] | 33.28 (0.2, 13.83%) [2/2] | 33.35 (0.27, 18.74%) [2/2] | 33.76 (0.03, 2.06%) [2/2] | 34.15 (0.72, 52.75%) [2/2] | 33.45 (0.53, 37.72%) [16/16] |
| SS16 | 5.10E+00 | 34.71 (0.35, 24.44%) [4/4] | 33.88 (0.04, 2.75%) [2/2] | 34.29 (0.28, 19.45%) [2/2] | 35.18 (0.82, 61.23%) [2/2] | 34.36 (0.26, 18.04%) [2/2] | 35.01 (1.32, 113.23%) [2/2] | 34.95 (0.27, 18.74%) [2/2] | 34.64 (0.61, 43.89%) [16/16] |
| SS17 | 2.55E+00 | 35.18 (0.39, 27.33%) [4/4] | 34.24 (0.57, 40.78%) [2/2] | 35.29 (0.53, 37.72%) [2/2] | 35.66 (0.48, 33.95%) [2/2] | 35.1 (0.09, 6.2%) [2/2] | 34.96 (0.2, 13.83%) [2/2] | Not Tested | 35.09 (0.52, 36.96%) [14/14] |
| SS18 | 1.28E+00 | 36.39 (0.51, 36.2%) [4/4] | 35.82 (0.96, 73.97%) [2/2] | 36.26 (0.44, 30.99%) [2/2] | 36.41 (0.91, 69.29%) [2/2] | 34.89 (0.37, 25.88%) [2/2] | 35.38 (0.75, 55.25%) [2/2] | Not Tested | 35.93 (0.77, 56.93%) [14/14] |
| SS19 | 6.38E-01 | 37.04 (0.84, 62.99%) [26/36] | 37.89 (0.03, 2.06%) [2/2] | 37.13 (0.8, 59.5%) [15/16] | 37.43 (0.96, 73.97%) [12/16] | 35.92 (0.89, 67.46%) [16/16] | Not Detected | Not Tested | 36.9 (1.01, 78.8%) [71/88] |
| SS20 | 3.19E-01 | 37.44 (0.54, 38.48%) [31/56] | 37.75 (0, 0%) [2/2] | 37.55 (1.15, 93.3%) [12/18] | 37.86 (1.25, 104.68%) [7/18] | 37.82 (0.65, 47.06%) [10/18] | 37.73 (0.04, 2.75%) [2/2] | Not Tested | 37.58 (0.78, 57.78%) [64/114] |
| SS21 | 1.59E-01 | 38.01 (1.34, 115.77%) [19/64] | Not Detected | 37.74 (0.89, 67.46%) [5/16] | 38.27 (0.15, 10.35%) [3/16] | 38.31 (0.8, 59.5%) [9/16] | Not Detected | Not Tested | 38.07 (1.09, 86.9%) [36/116] |
| SS22 | 7.97E-02 | 38.06 (0.18, 12.43%) [10/44] | 37.66 (NA, NA%) [1/2] | 37.8 (0.38, 26.6%) [4/16] | 37.54 (0.83, 62.11%) [5/16] | 38.16 (0.94, 72.08%) [7/16] | 35.23 (0.09, 6.2%) [2/2] | Not Tested | 37.75 (0.92, 70.21%) [29/96] |

FIG. 3

| Sample | Extraction Concentration (copies/ul) | Day 1 | Day 2 | Day 3 | Day 4 | Day 5 | Day 6 | Data |
|---|---|---|---|---|---|---|---|---|
| SS1 | 1.31E+08 | Not Tested | 7.78 (0.1, 6.89%) [3/3] | 7.8 (0.29, 20.16%) [3/3] | 8 (0.06, 4.13%) [2/2] | Not Tested | Not Tested | 7.84 (0.19, 13.13%) [8/8] |
| SS3 | 1.31E+06 | 15.48 (0.06, 4.13%) [2/2] | 15.29 (0.07, 4.82%) [3/3] | Not Tested | 15.25 (0.31, 21.58%) [2/2] | Not Tested | Not Tested | 15.33 (0.17, 11.74%) [7/7] |
| SS5 | 1.31E+04 | 22.17 (0.12, 8.27%) [2/2] | 22.5 (0.06, 4.13%) [3/3] | 22.55 (0.31, 21.58%) [3/3] | 22.71 (0.3, 20.87%) [2/2] | Not Tested | 21.46 (0.12, 8.27%) [3/3] | 22.25 (0.51, 36.2%) [13/13] |
| SS7 | 1.31E+02 | 28.79 (0.05, 3.44%) [2/2] | 29.5 (0.17, 11.74%) [3/3] | Not Tested | 28.88 (0.11, 7.58%) [2/2] | Not Tested | Not Tested | 29.12 (0.37, 25.88%) [7/7] |
| SS9 | 6.53E+01 | 29.92 (0, 0%) [2/2] | 30.07 (0.06, 4.13%) [3/3] | 30.54 (0.44, 30.99%) [3/3] | 30.09 (0.03, 2.06%) [2/2] | Not Tested | 30.06 (0.44, 30.99%) [3/3] | 30.16 (0.34, 23.72%) [13/13] |
| SS10 | 3.27E+01 | 30.91 (0.06, 4.13%) [2/2] | 31.22 (0.09, 6.2%) [3/3] | 31.16 (0.15, 10.35%) [3/3] | 31.34 (0.06, 4.13%) [2/2] | Not Tested | Not Tested | 31.16 (0.17, 11.74%) [10/10] |
| SS11 | 1.63E+01 | Not Tested | 31.93 (0.13, 8.96%) [3/3] | 32.79 (0.08, 5.51%) [3/3] | 32.24 (0.03, 2.06%) [2/2] | Not Tested | 32.68 (0.47, 33.21%) [2/2] | 32.4 (0.42, 29.52%) [10/10] |
| SS12 | 8.17E+00 | 32.7 (0.2, 13.83%) [2/2] | 33.06 (0.14, 9.66%) [2/2] | 33.62 (0.08, 5.51%) [3/3] | 33.77 (0.25, 17.33%) [2/2] | Not Tested | Not Tested | 33.32 (0.46, 32.46%) [9/9] |
| SS13 | 4.08E+00 | 33.75 (0.04, 2.75%) [2/2] | 34.13 (0.47, 33.21%) [4/4] | 35.8 (0.51, 36.2%) [6/6] | 35.27 (0.75, 55.25%) [4/4] | 33.12 (0.45, 31.72%) [6/6] | Not Tested | 34.48 (1.2, 98.87%) [22/22] |
| SS14 | 2.04E+00 | 34.97 (0.43, 30.25%) [2/2] | 35.14 (0.11, 7.58%) [5/5] | 35.32 (0.31, 21.58%) [7/7] | 35.24 (0.32, 22.29%) [4/4] | 34.57 (0.36, 25.16%) [6/6] | Not Tested | 35.05 (0.41, 28.78%) [24/24] |
| SS15 | 1.02E+00 | 35.28 (0.12, 8.27%) [2/2] | 36.59 (0.7, 51.1%) [4/4] | 36.76 (0.73, 53.58%) [7/7] | 36.78 (0.14, 9.66%) [3/3] | 35.68 (1.11, 89%) [6/6] | Not Tested | 36.3 (0.92, 70.21%) [22/22] |
| SS16 | 5.10E-01 | 36.01 (0.09, 6.2%) [2/2] | 37.35 (0.4, 28.06%) [3/4] | Not Tested | 37.29 (1.05, 82.8%) [2/3] | 36.97 (0.94, 72.08%) [3/5] | Not Tested | 36.96 (0.79, 58.64%) [10/18] |
| SS17 | 2.55E-01 | 38.87 (NA, NA%) [1/2] | 37.01 (0.44, 30.99%) [2/4] | Not Tested | 37.92 (NA, NA%) [1/3] | Not Tested | Not Tested | 37.7 (0.92, 70.21%) [4/13] |
| SS18 | 1.28E-01 | 36.97 (0.54, 38.48%) [2/2] | 37.32 (NA, NA%) [1/4] | Not Tested | Not Tested | Not Tested | Not Tested | 37.08 (0.43, 30.25%) [3/13] |
| SS20 | 3.19E-02 | Not Tested | 38.31 (NA, NA%) [1/2] | Not Tested | Not Tested | Not Tested | Not Tested | 38.31 (NA, NA%) [1/7] |

FIG. 5

| Concentration (ng/ul) | Day 1 | Day 2 | Day 3 | Day 4 | Day 5 | Data |
|---|---|---|---|---|---|---|
| 15 | 24.43 (0.41, 28.78%) [3/3] | 22.49 (1.14, 92.22%) [5/5] | 23.57 (NA, NA%) [1/1] | Not Tested | Not Tested | 23.26 (1.26, 105.87%) [9/9] |
| 5 | 26.36 (0.15, 10.35%) [3/3] | 24.47 (0.16, 11.04%) [5/5] | 25.22 (0.15, 10.35%) [5/5] | Not Tested | 24.87 (0.08, 5.51%) [3/3] | 25.14 (0.69, 50.29%) [16/16] |
| 1.6 | 28.06 (0.08, 5.51%) [3/3] | 26.81 (0.02, 1.38%) [5/5] | 27.04 (0.07, 4.82%) [5/5] | Not Tested | Not Tested | 27.19 (0.51, 36.2%) [13/13] |
| 0.56 | 29.84 (0.09, 6.2%) [3/3] | 29.16 (0.38, 26.6%) [5/5] | 28.79 (0.38, 26.6%) [5/5] | 28.43 (0.52, 36.96%) [8/8] | 27.91 (0.05, 3.44%) [3/3] | 28.77 (0.67, 48.67%) [24/24] |
| 0.18 | 31.24 (0.27, 18.74%) [3/3] | 31.26 (0.26, 18.04%) [5/5] | 30.36 (0.29, 20.16%) [5/5] | 30.51 (1.2, 98.87%) [8/8] | 29.52 (0.26, 18.04%) [3/3] | 30.6 (0.89, 67.46%) [24/24] |
| 0.062 | 32.79 (0.17, 11.74%) [3/3] | 33.5 (0.58, 41.56%) [5/5] | 32.27 (0.46, 32.46%) [5/5] | 31.74 (1, 77.82%) [8/8] | Not Tested | 32.43 (0.98, 75.88%) [21/21] |
| 0.02 | 33.82 (0.35, 24.44%) [2/3] | 35.18 (0.64, 46.26%) [4/5] | 33.21 (0.21, 14.53%) [5/5] | Not Tested | Not Tested | 34.04 (1.02, 79.79%) [11/13] |
| 0.006 | 35.99 (0.75, 55.25%) [3/3] | Not Tested | 35.34 (NA, NA%) [1/5] | Not Tested | Not Tested | 35.83 (0.69, 50.29%) [4/13] |

FIG. 7

METHODS AND KITS FOR THE DETECTION OF SARS-CoV-2

CROSS-REFERENCE TO RELATED APPLICATIONS

This application claims the benefit of U.S. Provisional Application No. 63/251,030 entitled "Methods and Kits for the Detection of SARS-Cov-2" which was filed Sep. 30, 2021, the entire disclosure of which is hereby incorporated herein by this reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 13,567 byte XML file named "91482-259US-PAT" created on Sep. 23, 2022.

TECHNICAL FIELD

The present invention relates to the field of detection of coronavirus, and more particularly, severe acute respiratory syndrome coronavirus 2 (SARS-CoV-2), which has been implicated in the pathogenesis of the disease COVID-19.

BACKGROUND

The world is experiencing a global outbreak of coronavirus disease COVID-19, first reported in China in December 2019. To date, over 609 million cases of COVID-19 have been reported globally. COVID-19 is a respiratory disease that causes flu-like symptoms, and can lead to pneumonia or more severe conditions. The strain of coronavirus (CoV) that causes the COVID-19 disease is referred to as severe acute respiratory syndrome coronavirus 2 (SARS-CoV-2). The virus, SARS-CoV-2, is a member of the Betacoronavirus (beta-CoV) genus, which includes other human coronaviruses such as CoV-SARS (2002-2003), CoV-MERS (2012), CoV-OC43, and CoV-HKU1. Additionally, other strains of coronaviruses in the Alphacoronavirus (alpha-CoV) genus known to infect humans include CoV-229E and CoV-NL63. The symptoms caused by infection with these human Alphacoronaviruses range from mild to severe respiratory illness. COVID-19 has spurred thousands of studies that have used a variety of patient outcome measures, many of which focus on time to recovery, blood tests, and/or viral load dynamics (Beigel 2020, Recovery Collaborative Group 2021, Gottlieb 2021).

Viral load has been a common measure within clinical trials and scientific investigations, yet, the methods for viral load determination have varied across studies. Viral load has commonly been assessed using SARS-CoV-2 RT-PCR Cq values (Shen 2020, Piubelli 2021, Zhou 2020,). A technique that could prove dangerous, as some studies do not consider inter-assay variation (Han 2021) or variation within collections (Dahdouh 2020). Another common method applies interpolation across a linear range of a SARS-CoV-2 RT-qPCR assay with a standard curve to calculate the number of viral particles within a sample (Gottlieb 2021, Cao 220, Pan 2020, Caillard 2020). This method provides a simple means to estimate viral particle quantity within a sample, however, it does not account for potential variation in sample collections across time or among patients, an aspect that could add significant variation when attempting to make statistical comparisons across time or between patients.

A need exists for more accurate assays to diagnose patients with suspected SARS-CoV-2, to aid in COVID-19 diagnosis, and for future surveillance and epidemiology. Current quantitative SARS-CoV-2 assays do not utilize DNA normalization.

SUMMARY

The present disclosure demonstrates that DNA normalization reduces the amount of variation due to sample collection differences within and between patients. The present invention uses normalization of SARS-CoV-2 viral load via RT-qPCR to provide higher-resolution data for comparison across time and between patients. The present invention serves as a method to allow quantification of both a SARS-CoV-2 target and a human DNA target allowing for viral normalization to the amount of DNA present in the sample. This provides a more accurate estimate of viral load across patients and time.

Here, investigators have used a viral real-time RT-qPCR assay and a second real-time qPCR assay to target human nucleic acids with a delta Cq analysis (Dahdouh 2020, Liu 2020), to account for variations in collections within a patient. One benefit of this method is that it is simple and accounts for sample variation (Dahdouh 2020, Schmittgen 2008); however, RNA expression across time, cells, and individuals can add variability into these analyses (Dahdouh 2020, Jacob 2013, Kozera 2013).

To further investigate these potential sources of variation, we performed a retrospective analysis of nasopharyngeal samples submitted for SARS-CoV-2 testing to our clinical laboratory. In addition to SARS-CoV-2 detection our clinical test utilized a RNase P RT-PCR assay to assess sample quality. This retrospective analysis was limited to patients who had been tested across at least 4 time points (mean: 7.7, median: 8), and in total included 217 patients and 1,611 nasopharyngeal sample collections. Across all samples, a range of 13.2 Cq was observed in the RNase P signal, suggesting a ~9,500-fold range in the concentration of host DNA and RNA across samples. However, within a single patient and across time, variation was lower, with a mean range of 5.0 (median: 4.98) Cq values, translating to a ~32-fold range. These data reveal drastic differences in the amount of host DNA and RNA collected between and within individuals across time, suggesting that variation in sampling could impact results and normalization of viral load to the amount of human DNA present within the sample would provide a valuable increase in the accuracy of viral load estimates.

In some aspects, the present invention relates to a Quantitative SARS-CoV-2 assay which utilizes parallel RNA and DNA extractions to quantify the concentration of SARS-CoV-2 and human DNA within a sample, allowing for viral normalization to the amount of host DNA collected in a specimen. This approach allows for normalization across sample collections in order to appropriately compare viral load (measured as viral copies/ng human DNA) across and between patients, without relying on stable RNA expression among patients, a common challenge in RT-PCR experiments. With this assay, we investigated the importance of sample collection and sample normalization in SARS-CoV-2-positive nasopharyngeal samples, and compared viral concentration (SARS-CoV-2 target copies per uL transport media) to normalized viral load (SARS-CoV-2 target copies per ng human DNA).

In some embodiments, the disclosure concerns methods, kits, and oligonucleotides used in the detection of the coronavirus strain, severe acute respiratory syndrome coronavirus 2 (SARS-CoV-2), are disclosed. In some aspects, the oligonucleotides are primers or probes used in the described methods or kits. In certain embodiments, the oligonucleotide consists of 40 or less nucleotides and has a nucleotide sequence that consists essentially of, or is a variant of, the nucleotide sequence of: SEQ ID NO:7, SEQ ID NO:8, SEQ ID NO:9, or SEQ ID NO:10.

In some aspects, the disclosure concerns methods of detecting severe acute respiratory syndrome coronavirus 2 (SARS-CoV-2) in a subject, comprising: adding to a mixture containing a sample from the subject, (a) a first primer comprising SEQ ID NO:7, (b) a second primer comprising SEQ ID NO:8, (c) a third primer comprising SEQ ID NO:9, and (d) a fourth primer comprising SEQ ID NO:10; subjecting the mixture to conditions that allow nucleic acid amplification to produce nucleic acid amplification products; and detecting the presence or absence of SARS-CoV-2 by analyzing the nucleic acid amplification products.

In some embodiments, is a nasopharangeal sample. Some nasopharangeal samples are placed in phosphate buffered saline (PBS), viral transport media (VTM) or universal transport medium (UTM).

In certain embodiments, the nucleic acid amplification utilizes polymerase chain reaction (PCR).

In some embodiments, both RNA and DNA in the sample are amplified, SARS-Cov-2 RNA and human DNA are quantified, SARS-Cov-2 viral load is normalized by comparison with human DNA load in the specimen.

Samples may comprise one or more of miRNA, tRNA, siRNA, mRNA, cDNA, genomic DNA sequences, single-stranded DNA, or complementary sequences thereof.

In certain embodiments, detecting the presence or absence of SARS-CoV-2 comprises incorporation of a probe into the amplification products. Any suitable probe may be utilized. Some probes are fluorescent dyes incorporated into the nucleic acid amplification products. In some embodiments, the fluorescent signal is monitored with each cycle of PRC.

In some embodiments, the detecting the presence or absence of SARS-CoV-2 is quantitative.

Other aspects of the disclosure concern methods of performing a quantitative viral determination comprising amplifying viral RNA and animal host DNA obtained in a sample from an animal to produce an amplified sample, quantifying concentrations of the viral and human host DNA within the amplified sample, and normalizing the amount of viral DNA by comparison with the amount of animal host DNA in the amplified sample. In some embodiments, the viral determination is a SARS-Cov-2 assay.

In some embodiments, human host DNA and viral RNA are isolated, purified and concentrated separately, and amounts of human host DNA and viral RNA are quantified.

In yet other aspects, the disclosure concerns kits comprising (a) a first primer comprising SEQ ID NO:7, (b) a second primer comprising SEQ ID NO:8, (c) a third primer comprising SEQ ID NO:9, and (d) a fourth primer comprising SEQ ID NO:10.

The foregoing features and elements may be combined in various combinations without exclusivity, unless expressly indicated otherwise. These features and elements as well as the operation thereof will become more apparent in light of the following description. It should be understood, however, the following description is intended to be exemplary in nature and non-limiting.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the figures, wherein like numerals may denote like elements.

FIG. 3 illustrates results of SARS-CoV-2 synthetic control quantification and linear range across all validation days (Mean, (SD, % CV) [n amplified/total]).

FIG. 5 illustrates results of SARS-CoV-2 assay validation and linear range across all validation days (Mean, (SD, % CV) [n amplified/total]).

FIG. 7 illustrates results of DNA RNase P assay validation and linear range across all validation days (Mean, (SD, % CV) [n amplified/total]).

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention

DETAILED DESCRIPTION

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements. As used herein, the term "comprise," and conjugations or any other variation thereof, are used in its non-limiting sense to mean that items following the word are included, but items not specifically mentioned are not excluded.

The disclosed method uses nasopharangeal samples in PBS, VTM, or UTM to quantify both the number of viral target copies and the amount of human DNA present within the sample. DNA and RNA are isolated, purified, and concentrated separately. The RNA is used to quantify SARS-CoV-2 viral concentrations using a the disclosed RT-qPCR assay targeting the SARS-CoV-2 N gene. The DNA is used to quantify the amount of human DNA within 100 ul of material using the RNase P target. Both the SARS-CoV-2 and RNase P targets are quantified by interpolating the concentration through Cq values and a standard curve. Finally, viral concentration is normalized to the human DNA concentration producing the viral load of the sample (genome copies per ng Human target).

Figure 1:
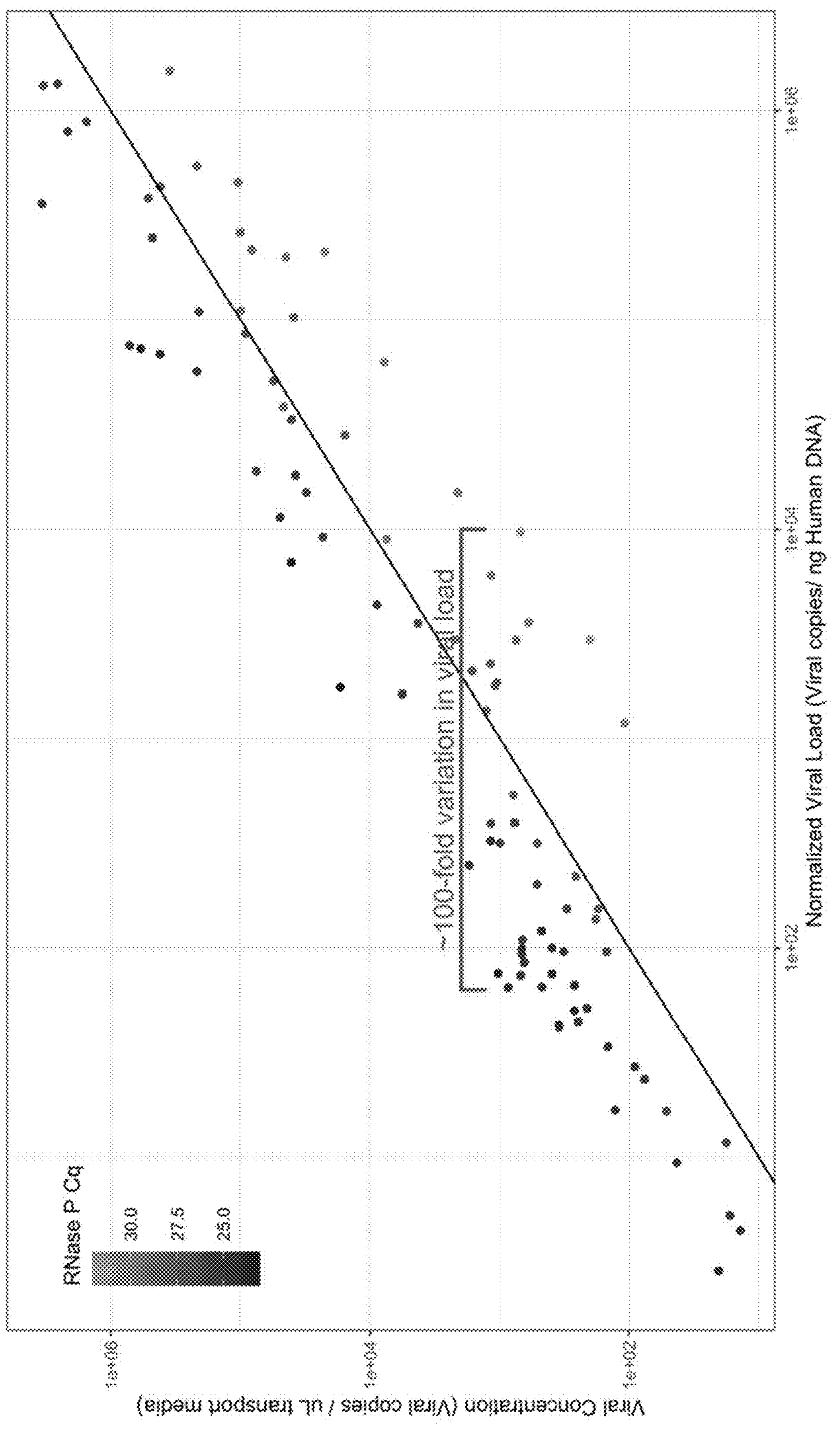
FIG. 1 illustrates the linear relationship between viral concentration and normalized viral load (Pearson=0.75, Spearman=0.92); Dotted rectangle includes samples with similar viral concentration, yet normalized viral loads have a 100-fold range.

To investigate the impacts of normalization, 94 samples were quantified using the disclosed Quantitative SARS-CoV-2 assay which pairs a quantitative SARS-CoV-2 N gene assay (RNA), with a quantitative human RNase P assay (DNA). By pairing these quantitative assays, the investigator captures the viral concentration (viral copies/ul transport media) using the SARS-CoV-2 N gene assay and the amount of human DNA (ng/ul) within a sample using the RNase P assay. Viral concentration was normalized to the amount of human DNA in a sample, producing a normalized viral load (viral copies/ng human DNA), the original viral concentration was then compared to the normalized viral load. Overall, a strong linear relationship (Pearson Correlation=0.75, Spearman Correlation=0.92) was observed between the measures (FIG. 1) and viral concentration explained 56% of the variability within the viral load. These results suggest that viral concentration is highly correlated to the normalized viral load at broad scales, yet, at finer scales a high amount of variability is seen between viral concentration and viral load. For example, samples with a viral concentration of $\sim 1\times 10^3$ copies per ul had a normalized viral load that ranged from $\sim 1\times 10^2$ to $1\times 10^4$ copies per ng Human DNA, translating to a 100-fold variation within the viral load (FIG. 1).

These data emphasize the importance of normalizing results with a host-specific assay in studies that utilize viral load to investigate SARS-CoV-2 and other viral infections. While quantitative normalization may not be worth the higher cost when the goal of a study is to characterize drastic differences in viral concentrations (although there are semi-quantitative methods that allow for inexpensive host normalization that should be considered), when high-resolution data are needed to quantify differences across treatments or viral dynamics across individuals, normalization would play a critical role in resolving differences between groups. For example, across individuals' samples with the same viral concentration corresponded to a 100-fold range of normalized viral loads, an impact that would increase the variance within experiments and impact the statistical interpretations of the study. Importantly, reduction in the variance within experiments influences sample size calculations, potentially reducing the number of samples required, a critical component as COVID-19 cases fall and recruitment and sample acquisition becomes more difficult, which can in turn reduce associated costs. Overall, the emergence of SARS-CoV-2 has challenged the scientific community to develop better diagnostics, vaccines, and treatments in record time. As SARS-CoV-2 vaccinations increase and COVID-19 cases decrease, it is important to begin translating the scientific advancements that were made as a result of the pandemic to other diseases to take advantage of the hard-won technological achievements of the 2020 pandemic.

The terms "animal" refers to any member of the animal kingdom. In some embodiments, animals typically have the ability to move and do not have cell walls made of cellulose. The term includes humans. The term "animal host" refers to animals that play host to the virus.

As used herein, "amplification reaction" refers to a method of detecting target nucleic acid by in vitro amplification of DNA or RNA.

As used herein, "polymerase chain reaction (PCR)" refers to the amplification of a specific DNA sequence, termed target or template sequence, that is present in a mixture, by adding two or more short oligonucleotides, also called primers, that are specific for the terminal or outer limits of the template sequence. The template-primers mixture is subjected to repeated cycles of heating to separate (melt) the double-stranded DNA and cooling in the presence of nucleotides and DNA polymerase such that the template sequence is copied at each cycle.

The term "primer" refers to DNA oligonucleotides complementary to a region of DNA and serves as the initiation of amplification reaction from the 5' to 3' direction.

The term "primer pair" refers to the forward and reverse primers in an amplification reaction leading to amplification of a double-stranded DNA region of the target.

The term "target" refers to a nucleic acid region bound by a primer pair that is amplified through an amplification reaction.

The PCR "product" or "amplicon" is the amplified nucleic acid resulting from PCR of a set of primer pairs.

The term "multiplex amplification reaction" herein refers to the detection of more than one template in a mixture by the addition of more than one set or pair of oligonucleotide primers.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out. The amplification process may result in the production of one or more nucleic acid amplification products, or amplicons.

The term "template" refers to nucleic acid originating from a sample that is analyzed for the presence of one or more markers. In contrast, "background template" or "control" is used in reference to nucleic acid other than sample template that may or may not be present in a sample. A presence of background template is most often inadvertent. It may be the result of carryover, or it may be due to the presence of nucleic acid contaminants sought to be purified out of the sample. For example, nucleic acids from organisms other than those to be detected may be present as background in a test sample.

The term "amplifiable nucleic acid" refers to nucleic acids that may be amplified by any amplification method. It is contemplated that "amplifiable nucleic acid" will usually comprise "sample template." The terms "PCR product," "PCR fragment," "amplification product," and "amplicon" refer to the resultant mixture of compounds after two or more cycles of the PCR steps of denaturation, annealing and extension. These terms encompass the case where there has been amplification of one or more segments of one or more target sequences.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting a marker. Nucleic acid sequences may be identified by the IUAPC letter code which is as follows: A=Adenine base; C=Cytosine base; G=guanine base; T or U=thymine or uracil base; I=inosine base. M=A or C; R=A or G; W=A or T; S=C or G; Y=C or T; K=G or T; V=A or C or G; H=A or C or T; D=A or G or T; B=C or G or T; N or X=A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence.

In some embodiments, the present invention comprises a method of detecting SARS-CoV-2 in a subject, comprising the steps of contacting a sample obtained from the subject with, (a) a first primer comprising SEQ ID NO:7, (b) a second primer comprising SEQ ID NO:8, (c) a third primer comprising SEQ ID NO:9, and (d) a fourth primer comprising SEQ ID NO:10. The method may further include the steps of carrying out quantitative RT-qPCR.

Generally, some embodiments of the present invention can be used to detect, identify, assess, sequence, or otherwise evaluate a marker. A marker may be any molecular structure produced by a cell, expressed inside the cell, accessible on the cell surface or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, single-stranded DNA, or complementary sequences thereof.

In some aspects, the markers may include one or more sets of amplifiable nucleic acids that can provide diagnostic information about the pathogen. For example, the markers may include amplifiable nucleic acid sequences that can be used to assess the presence and/or absence of one or more pathogen that may have the potential to cause a diseased state in the subject. In some embodiments, the markers may include amplifiable nucleic acid sequences that can be used to identify one or more of the following exemplary microorganisms and/or viruses: coronavirus (including but not limited to SARS-CoV-2). In some embodiments, the methods may include the use of one or more than one marker per virus.

After selection of the markers, marker-specific primers/oligonucleotides can be designed for the amplification of the markers to produce the desired amplicons, as detailed above. As is known in the art, a forward and a reverse marker-specific primer can be designed to amplify the marker from a nucleic acid sample. In some embodiments, the forward and reverse primers can be designed to produce an amplicon (e.g., some or all of the sequence of the marker) of a desired length. For example, the length of the amplicon may comprise approximately 50 base pairs (bp), 70 bp, 80 bp, 90 bp, 100 bp, 150 bp, 200 bp, 250 bp, 300 bp, 350 bp, 400 bp, 450 bp, 500 bp, 1,000 bp, or any size amplicon greater in size or therebetween.

Moreover, in some embodiments, one or more of the markers can be amplified in a multiplex manner. For example, in some aspects, nucleic acids can be obtained from the sample and the oligonucleotides used to amplify one or more of the markers used to identify the strain of the virus can be added to a single mixture to produce a plurality of amplicons in a single reaction mixture. In other aspects, the oligonucleotides can be added to multiple mixtures to provide for the creation of multiple amplicons in multiple mixtures. In some aspects, amplification of the markers used to identify virus/diagnose an infection can also occur in a multiplex manner such that some or all of the amplicons are generated in a single reaction for a particular sample. In other aspects, amplification of the markers used to identify virus/diagnose an infection can occur in multiple reaction vessels. Overall, as described in greater detail below, regardless of the multiplex nature of some embodiments of the invention, after amplification of the markers, the method may include processing and sequencing the resulting amplicons to provide information related to the identification, characterization, and strain identity of one or more viruses that may be present within the sample.

Some embodiments of the invention may comprise the use of one or more methods of amplifying a nucleic acid-based starting material (i.e., a template, including genomic DNA, crude DNA extract, single-stranded DNA, double-stranded DNA, cDNA, RNA, or any other single-stranded or double-stranded nucleic acids). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with QB replicase, whole genome amplification with enzymes such as @29, whole genome PCR, in vitro transcription with T7 RNA polymerase or any other RNA polymerase, or any other method by which copies of a desired sequence are generated. Any suitable amplification method may be utilized.

PCR generally involves the mixing of a nucleic acid sample, two or more primers or oligonucleotides (primers and oligonucleotides are used interchangeably herein) that are designed to recognize the template DNA, a DNA polymerase, which may be a thermostable DNA polymerase such as Taq or Pfu, and deoxyribose nucleoside triphosphates (dNTP's). In some embodiments, the DNA polymerase used can comprise a high fidelity Taq polymerase such that the error rate of incorrect incorporation of dNTPs is less than one per 1,000 base pairs. Reverse transcription PCR (RT-PCR), real time reverse transcription PCR (rRT-PCR), quantitative reverse transcription PCR (RT-qPCR or quantitative RT-qPCR), and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified template. In such analyses, incorporation of fluorescent dye into the amplified strands may be detected or measured.

Either primers or primers along with probes allow a quantification of the amount of specific template DNA present in the initial sample. In addition, RNA may be detected by PCR analysis by first creating a DNA template from RNA through a reverse transcriptase enzyme (i.e., the creation of cDNA). The marker expression may be detected by quantitative PCR analysis.

Detection according to some embodiments of the disclosure may comprise contacting the amplified nucleic acid with a probe; and detecting the hybridization of probe with the amplified nucleic acid. Detection may be performed by a variety of methods, such as but not limited to, by a nucleic acid amplification reaction. In some embodiments the amplification reaction maybe an end-point determination or the amplification reaction maybe quantitative. The quantification may be a real time reverse transcription PCR (rRT-PCR) method. In some embodiments, the real-time PCR may be a SYBR® Green Assay or a TAQMAN® Assay. Detection, in various embodiments, maybe performed by hybridization using probes specific to target sequences. According to various embodiments, combinations of amplification and hybridization may be used for detection.

As used herein, "real-time PCR" (sometimes referred to as "qPCR") may refer to the detection and quantitation of a DNA or a surrogate thereof in a sample. In some embodiments, the amplified segment or "amplicon" can be detected in real time using a 5'-nuclease assay, particularly the TaqMan® assay as described by e.g., Holland et al. (Proc. Natl. Acad. Sci. USA 88:7276-7280, 1991); and Heid et al. (Genome Research 6:986-994, 1996). For use herein, a TaqMan® nucleotide sequence to which a TaqMan® probe binds can be designed into the primer portion, or known to be present in DNA of a sample. In some embodiments, the PCR methods use end-point PCR and a positive result is obtained when there is a detectable signal after the PCR is finished. Real-time and end-point PCR methods useful in accordance with the present methods and compositions include, but are not limited to, fluorescence resonance energy transfer (FRET), TAQMAN®, Molecular Beacons, Amplifluor®, Scorpion™, Plexor™, BHQplus™ (a modified non-fluorescent dark quencher dye), BHQ-1TM (a non-fluorescent dark quencher dye).

When a TaqMan® probe is hybridized to DNA or a surrogate thereof, the 5'-exonuclease activity of a thermostable DNA-dependent DNA polymerase such as SUPER-TAQ® (a Taq polymerase from *Thermus aquaticus*, Ambion, Austin, Tex.) digests the hybridized TaqMan® probe during the elongation cycle, separating the fluor from the quencher. The reporter fluor dye is then free from the quenching effect of the quencher moiety resulting in a decrease in FRET and an increase in emission of fluorescence from the fluorescent reporter dye. One molecule of reporter dye is generated for each new molecule synthesized, and detection of the free reporter dye provides the basis for quantitative interpretation of the data.

In real-time PCR, the amount of fluorescent signal is monitored with each cycle of PCR. Once the signal reaches a detectable level, it has reached the "threshold or cycle threshold (Ct)." A fluorogenic PCR signal of a sample can be considered to be above background if its Ct value is at least 1 cycle less than that of a no-template control sample. The term "Ct" represents the PCR cycle number when the signal is first recorded as statistically significant. Thus, the lower the Ct value, the greater the concentration of nucleic acid target. The term "Cq" designates quantification cycle and is interchangeable with the term "Ct" (See e.g., "MIQE: Minimum Information for Publication of Quantitative Real-Time PCR Experiments," Clinical Chemistry 55:4; 611-622 (2009). In the TaqMan® assay, typically each cycle almost doubles the amount of PCR product and therefore, the fluorescent signal should double if there is no inhibition of the reaction and the reaction was nearly 100% efficient with purified nucleic acid. Some systems conduct monitoring during each thermal cycle at a pre-determined or user-defined point.

Detection method embodiments using a TaqMan® probe sequence comprise combining the test sample with PCR reagents, including a primer set having a forward primer and a reverse primer, a DNA polymerase, and a fluorescent detector oligonucleotide TaqMan® probe, as well as dNTP's and a salt, to form an amplification reaction mixture; subjecting the amplification reaction mixture to successive cycles of amplification to generate a fluorescent signal from the detector probe; and quantitating the nucleic acid presence based on the fluorescent signal cycle threshold of the amplification reaction.

The following examples are given for purely illustrative and non-limiting purposes of the present invention.

EXAMPLES

The following describes how the disclosed SARS-CoV-2 Quantitative RT-qPCR test was performed and validated. The tests used nasopharyngeal samples (250 ul) in PBS, VTM, or UTM to quantify both the number of viral target copies and the amount of DNA present within the sample. DNA and RNA were isolated, purified, and concentrated separately. The RNA was used to quantify SARS-CoV-2 viral concentrations using a TGen developed RT-qPCR assay developed to target the N gene. The DNA was used to quantify the amount of human DNA within 100 ul of material using the RNase P target. Finally, both the SARS-CoV-2 and RNase P targets are quantified by interpolating the concentration through Cq values and a standard curve. Finally, viral concentration was normalized to the human DNA concentration producing the viral load of the sample (genome copies per ng human DNA).

Methods

Control Preparation

SARS-CoV-2 Positive Template Control

This procedure describes the procedures for synthesizing and quantifying SARS-CoV-2 control materials. The first step in this process is amplifying the target sequence from a plasmid and add a T7 promoter region. After successful amplification, the PCR product is purified with a 1× bead cleanup. The PCR product is then passed into an in-vitro RNA synthesis reaction using a T7 transcription kit. After RNA synthesis, the synthesized single stranded RNA is purified with a column-based purification kit. Finally, the RNA is quantified using Poisson limiting dilutions and working positive control stocks are created.

Target sequence amplification from plasmid. Steps of the process include the following steps. 100 μL working stock of primers (20× assay mixture) were created using the Table 1. Each vial was labeled and store in −20 C Freezer.

TABLE 1

SARS-CoV-2 Quantitative RT-qPCR primers.

| | Primer Sequence | Stock Conc. | Final Conc. | 20X Assay Mix. |
|---|---|---|---|---|
| For N Gene Target | | | | |
| 1_NF38 | CCCGCATTACGTTTGGTGGAC (SEQ ID NO: 1) | 100 μM | 20 μM | 25 μL |

TABLE 1-continued

SARS-CoV-2 Quantitative RT-qPCR primers.

| | Primer Sequence | Stock Conc. | Final Conc. | 20X Assay Mix. |
|---|---|---|---|---|
| T7_1_NR1154 | ATAGCTAATACGACTCACTAT AGGGCTCTGCGGTAAGGCTTGAGTT TCA (SEQ ID NO: 2) | 100 pμM | 20 μM | 25 μL |
| Molecular Grade Water | NA | NA | NA | 50 μL |
| For S Gene Target | | | | |
| RNA_Amp_CoV-2_S1-4_F | GTCCTTCCCTCAGTCAGCACC (SEQ ID NO: 3) | 100 μM | 20 μM | 25 μL |
| T7_RNA_Amp_ CoV-2_S1-4_R | ATAGCTAATACGACTCACTAT AGGGGCACTGGCTCAG AGTCGTCTT C (SEQ ID NO: 4) | 100 μM | 20 μM | 25 μL |
| Molecular Grade Water | NA | NA | NA | 50 μL |

In a template addition area, 2 μL of diluted N gene plasmid was added to the tube labeled N gene. Pipette mix.

```
N Gene (SEQ ID NO: 5):
ATGTCTGATAATGGACCCCAAAATCAGCGAAATGCACCCCGCATTACGT

TTGGTGGACCCTCAGATTCAACTGGCAGTAACCAGAATGGAGAACGCAG

TGGGGCGCGATCAAAACAACGTCGGCCCCAAGGTTTACCCAATAATACT

GCGTCTTGGTTCACCGCTCTCACTCAACATGGCAAGGAAGACCTTAAAT

TCCCTCGAGGACAAGGCGTTCCAATTAACACCAATAGCAGTCCAGATGA

CCAAATTGGCTACTACCGAAGAGCTACCAGACGAATTCGTGGTGGTGAC

GGTAAAATGAAAGATCTCAGTCCAAGATGGTATTTCTACTACCTAGGAA

CTGGGCCAGAAGCTGGACTTCCCTATGGTGCTAACAAAGACGGCATCAT

ATGGGTTGCAACTGAGGGAGCCTTGAATACACCAAAAGATCACATTGGC

ACCCGCAATCCTGCTAACAATGCTGCAATCGTGCTACAACTTCCTCAAG

GAACAACATTGCCAAAAGGCTTCTACGCAGAAGGGAGCAGAGGCGGCAG

TCAAGCCTCTTCTCGTTCCTCATCACGTAGTCGCAACAGTTCAAGAAAT

TCAGATCAGATCGCAACTCCAGGCAGCAGTAGGGGAACTTCTCCTGCTA

GAATGGCTGGCAATGGCGGTGATGCTGCTCTTGCTTTGCTGCTGCTTGA

CAGATTGAACCAGCTTGAGAGCAAAATGTCTGGTAAAGGCCAACAACAA

CAAGGCCAAACTGTCACTAAGAAATCTGCTGCTGAGGCTTCTAAGAAGC

CTCGGCAAAAACGTACTGCCACTAAAGCATACAATGTAACACAAGCTTT

CGGCAGACGTGGTCCAGAACAAACCCAAGGAAATTTTGGGGACCAGGAA

CTAATCAGACAAGGAACTGATTACAAACATTGGCCGCAAATTGCACAAT

TTGCCCCCAGCGCTTCAGCGTTCTTCGGAATGTCGCGCATTGGCATGGA

AGTCACACCTTCGGGAACGTGGTTGACCTACACAGGTGCCATCAAATTG

GATGACAAAGATCCAAATTTCAAAGATCAAGTCATTTTGCTGAATAAGC

ATATTGACGCATACAAAACATTCCCACCAACAGAGCCTAAAAAGGACAA

AAAGAAGAAGGCTGATGAAACTCAAGCCTTACCGCAGAGACAGAAGAAA
```

-continued

```
CAGCAAACTGTGACTCTTCTTCCTGCTGCAGATTTGGATGATTTCTCCA

AACAATTGCAACAATCCATGAGCAGTGCTGACTCAACTCAGGCCTAA
```

2 μL of the diluted S gene plasmid was added to the tube labeled S gene and mixed.

```
S1-4 gene (SEQ ID NO: 6):
GTCCTTCCCTCAGTCAGCACCTCATGGTGTAGTCTTCTTGCATGTGACT

TATGTCCCTGCACAAGAACCCCACTTCACAACTGCTCCTGCCATTTGTC

ATGATGGAAAAGCACACTTTCCTCGTGAAGGTGTCTTTGTTTCAAATGG

CACACACTGGTTTGTAACACAAAGGAATTTTTATGAACCACAAATCATT

ACTACAGACAACACATTTGTGTCTGGTAACTGTGATGTTGTAATAGGAA

TTGTCAACAACACAGTTTATGATCCTTTGCAACCTGAATTAGACTCATT

CAAGGAGGAGTTAGATAAATATTTTAAGAATCATACATCACCAGATGTT

GATTTAGGTGACATCTCTGGCATTAATGCTTCAGTTGTAAACATTCAAA

AAGAAATTGACCGCCTCAATGAGGTTGCCAAGAATTTAAATGAATCTCT

CATCGATCTCCAAGAACTTGGAAAGTATGAGCAGTATATAAAATGGCCA

TGGTACATTTGGCTAGGTTTTATAGCTGGCTTGATTGCCATAGTAATGG

TGACAATTATGCTTTGCTGTATGACCAGTTGCTGTAGTTGTCTCAAGGG

CTGTTGTTCTTGTGGATCCTGCTGCCCCCTTGATGAAGACGACTCTGAG

CCAGTGCTCAAAGGAGTCAAATTACATTACACATAA
```

In the remaining 2 tubes, 2 μL of molecular grade water was added and mixed. All four tubes were centrifuged for 30 seconds on a benchtop centrifuge. Tubes were placed into the Biorad T100 thermocycler.

PCR Product Purification

Ampure XP beads were allowed to come to room temperature and then 30 μL of Ampure XP beads were added to each PCR product and mixed. Samples were allowed to sit for 5 minutes and then placed on magnet for 5 minutes. The DNA attaches to the magnetic XP beads, which are held at the bottom of the tube by the magnet. 200 μL of 80% EtOH is then dispensed into each well and the sample was incubated for 30 seconds. The EtOH was carefully removed with the pipette. 200 μL of 80% EtOH was dispensed into each well and incubated for 30 seconds. The EtOH was removed with the pipette. All EtOH was removed and the beads were allowed to dry. The tubes were removed from the magnet. 30 μL molecular grade water was added to each sample and vortexed briefly. DNA was released from the XP beads. The tubes were placed on magnet for 3 minutes and the purified product was transferred to fresh tubes.

In-Vitro RNA Synthesis

A HiScribe T7 Quick High Yield RNA Synthesis Kit (New England Biolabs, Cat no. E2050S) was used to create the following reaction mixture for each tube.

Transcribed RNA Purification

Transcribed RNA was purified using Monarch RNA Cleanup Kit (500 μg) (New England Biolabs, Cat no. T2050S).

Generating SS0

24 dilution tubes were created with molecular grade water. Conduct qPCR analysis was conducted on all tubes (see TNCL-0801: SARS-CoV-2 RT-PCR). S gene and N gene should have CT values below 10. $N_{NTC}$ and $S_{NTC}$ should be >25. The dilution factor needed for S gene and N gene samples to produce a signal of ~7 CTs was calculated. S gene and N gene tubes were diluted accordingly. Equal parts diluted N2 and S4 products were combined to create a combined sample with CT value for each assay ~8 Cts.

RNA Target Quantification

PCR was run to determine CT value of SS0. Perform Poisson replicated on four concentrations.

Human RNase P Control

Quantified human RNase P signal were prepared for validation and standards.

Background Transport Media

RNase P positive SARS-CoV-2 negative background media was prepared for controls and assay validation. SARS-CoV-2 negative samples were pooled and tested with TNCL protocol in duplicate (extractions) with triplicate RT-qPCR assays to ensure media was negative.

Extractions 50 ul of DNA and 50 ul of RNA were extracted, purified and concentrated. At minimum the operator should include one negative extraction control (Molecular grade water in shield), one positive extraction control (SARS-CoV-2 Negative pooled media), and several samples with known concentrations. SARS-CoV-2 controls were generated by spiking in quantified synthetic target into SARS-CoV-2 negative PBS. Human DNA controls were prepared by diluting human genomic DNA to three concentrations and tested in triplicate.

RT-qPCR

The disclosed assay used the TGen N-2 (TG-N2) assay and the RNase P assay designed by the CDC. The TG-N2 assay quantified the viral concentration of the purified RNA, while the RNase P assay targeted human DNA within the purified DNA. This section covers the specifics of running the assay on the Biorad CFX Connect.

Assay Setup TG-N2: Reactions for the TG-N2 assay utilizes 10 ul reaction volumes using Biorad Reliance One-Step Multiplex RT-qPCR Supermix (Cat. No. 12010220). The TG-N2 assay utilized a forward primer (TTCAGCGTTCTTCGGAATGTC) (SEQ ID NO:7) and reverse primer (TGGCACCTGTGTAGGTCAAC) (SEQ ID No; 12) with a final concentration of 450 nM and a BHQ™ probe (CGCATTGGCATGGAAGTCACACC) (SEQ ID NO:8) with a final concentration of 150 nM.

Assay Setup CDC-RNase P: Reactions for the RNase P assay utilizes 10 ul reaction volumes using Biorad SsoAdvanced Universal Probes Supermix (Cat. No. 1725281). The RNase P assay utilized a forward primer (AGATTTGGACCTGCGAGCG) (SEQ ID NO:9) and reverse primer (GAGCGGCTGTCTCCACAAGT) (SEQ ID NO:10) with a final concentration of 450 nM and a BHQ™ probe (TTCTGACCTGAAGGCTCTGCGCG) (SEQ ID NO:11) with a final concentration of 150 nM.

Analysis

Control Performance

At minimum, a negative extraction control should be included with each run. This sample should be negative for both targets. Additionally, a positive extraction control (pooled NP PBS) should be used in the RNA extraction to confirm that the pool is negative for SARS-CoV-2. Since this is most often incorporates pooled clinical NP matrix, Cq values above 37 are also acceptable.

Statistical Interpretation

To calculate the viral load of a clinical sample, all associated plate controls must perform as expected and both replicates of the RNA TG-N2 assay and the DNA Rnase P assay must amplify and produce a Cq value. During validation, two linear models were produced to allow interpolation of viral concentration and human DNA. The TG-N2 assay consisted of a simple model that predicted the logarithmic viral concentration from the mean Cq value of the sample. The RNase P assay utilized a similar format but also included an offset of date to correct for inter assay variation. Interpolation values that fell outside of each assay's linear range were considered Validation Data The TG-N2 assay validation consisted of determining the Limit of Detection (LoD) and Limit of Quantification (LoQ) using the described SARS-CoV-2 Quantitative RT-qPCR Protocol. Several other validations including strain inclusivity and analytical specificity have been performed for this assay and are detailed in the TGen TNCL SARS-CoV-2 test documentation. Since the RNase P assay is a previously developed assay set, validation consisted of determining the Limit of Detection (LoD) and Limit of Quantification (LoQ) using the described SARS-CoV-2 Quantitative RT-qPCR Protocol. Control validation consisted of validating and quantifying the synthetic transcription product that was produced using the above protocol.

Control Validation

Synthetic transcription product was produced, diluted, and tested per the above procedures. The product was quantified using the Poisson distribution and a limiting dilution series (targets/reaction=−ln(negative reactions/total)) across four dilutions each with a sample size greater than 80 replicates. Additionally, the assay and product were assessed for linearity and assay efficiency using these data (Table 2).

TABLE 2

Results of Poisson calculations based on limiting dilution analysis.

| Dilution | negative/total | copies/rxn | copies/ul | copies/ul at SS19 |
|---|---|---|---|---|
| SS19 | 17/88 | 1.64 | 0.55 | 0.55 |
| SS20 | 50/114 | 0.82 | 0.27 | 0.55 |
| SS21 | 80/116 | 0.37 | 0.12 | 0.50 |
| SS22 | 67/96 | 0.35 | 0.12 | 0.95 |
| | Average SS19 | | | 0.64 |

A high rate of dropout was seen from SS19 to SS22, thus these dilutions were chosen as the dilutions for limiting dilution analysis. Concentrations (copies/rxn and copies/ul) were calculated for each dilution. Finally, each copies/ul was converted to the estimated SS19 concentration based on the number of dilutions between SS19 and the dilution in question; these estimates were than averaged to give a more accurate representation of the SS19 concentration (Averaged SS19 concentration: 0.64 copies/ul) (Table 2). The averaged SS19 estimate was then used to calculate concentrations for all of the remaining dilutions, which represents the concentration of N2 target per ul in each synthetic stock (Table 2).

Figure 2:
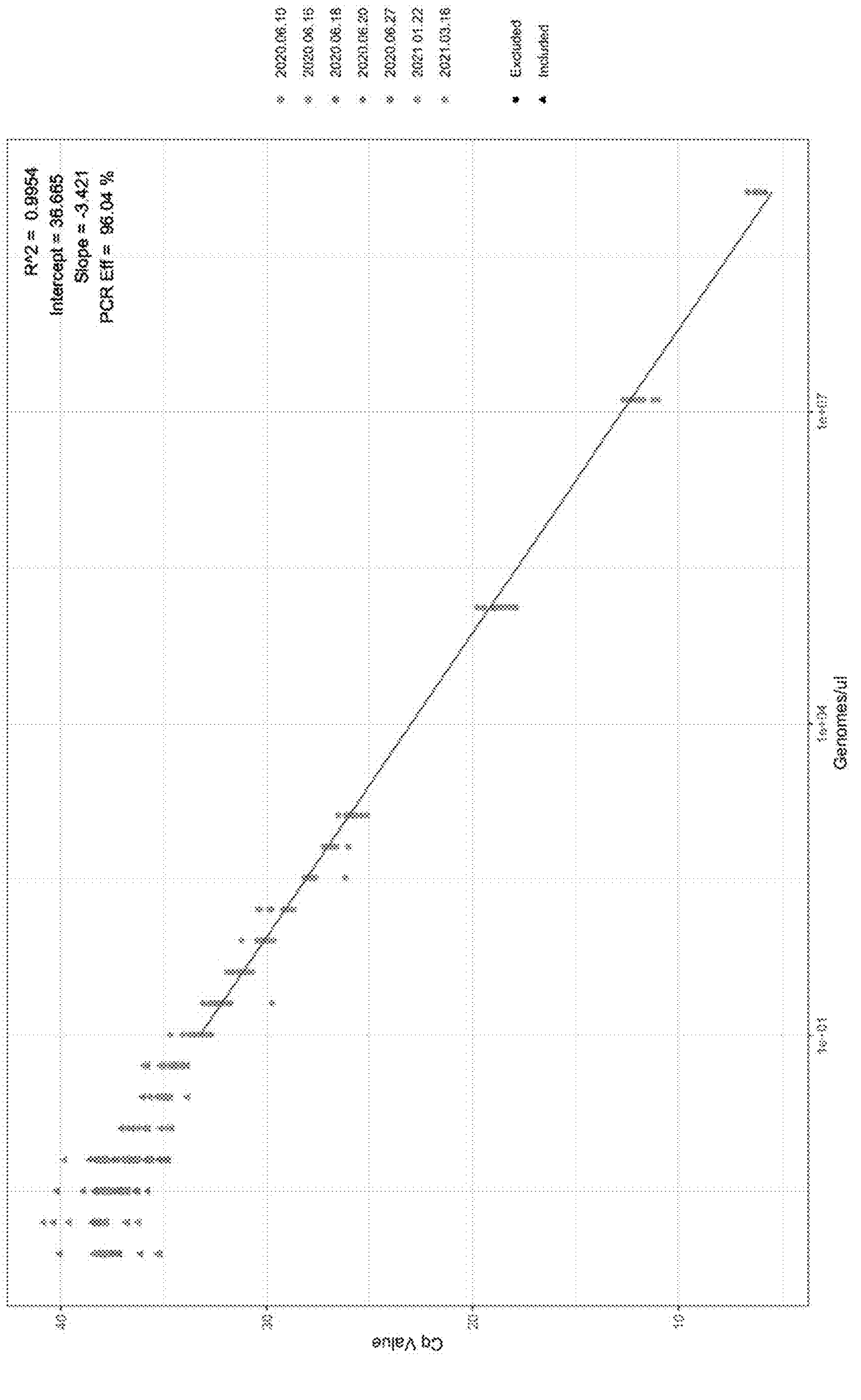
FIG. 2 illustrates SARS-CoV-2 positive template across days.

FIG. 2 shows the SARS-CoV-2 positive template across days. The assay efficiency using the synthetic product (concentration>10 copies/u;) and the TG-N2 assay was determined to be 96%. FIG. 3 presents results of SARS-CoV-2 synthetic control quantification and linear range across all validation days (Mean, (SD, % CV) [n amplified/total]). The LoD of the TG-N2 assay was determined to be 1.3 copies per ul (3.9 copies/rxn).

TG-N2 Validation

Quantified synthetic SARS-CoV-2 controls were diluted and spiked into negative SARS-CoV-2 nasopharyngeal swabs (PBS). This final dilution accounted for a 1:10 (1-part synthetic control, 9-parts PBS) decrease in concentration between the controls and extracted material. Extracted material was processed using the TGen North SARS-CoV-2 Quantitative RT-qPCR Protocol across several days. Using these data, the LoD and LoQ were determined. The LoD was determined to be 1.02 copies/ul and the LoQ was determined to be 8.2 copies/ul (FIG. 4 and FIG. 5).

Figure 4:
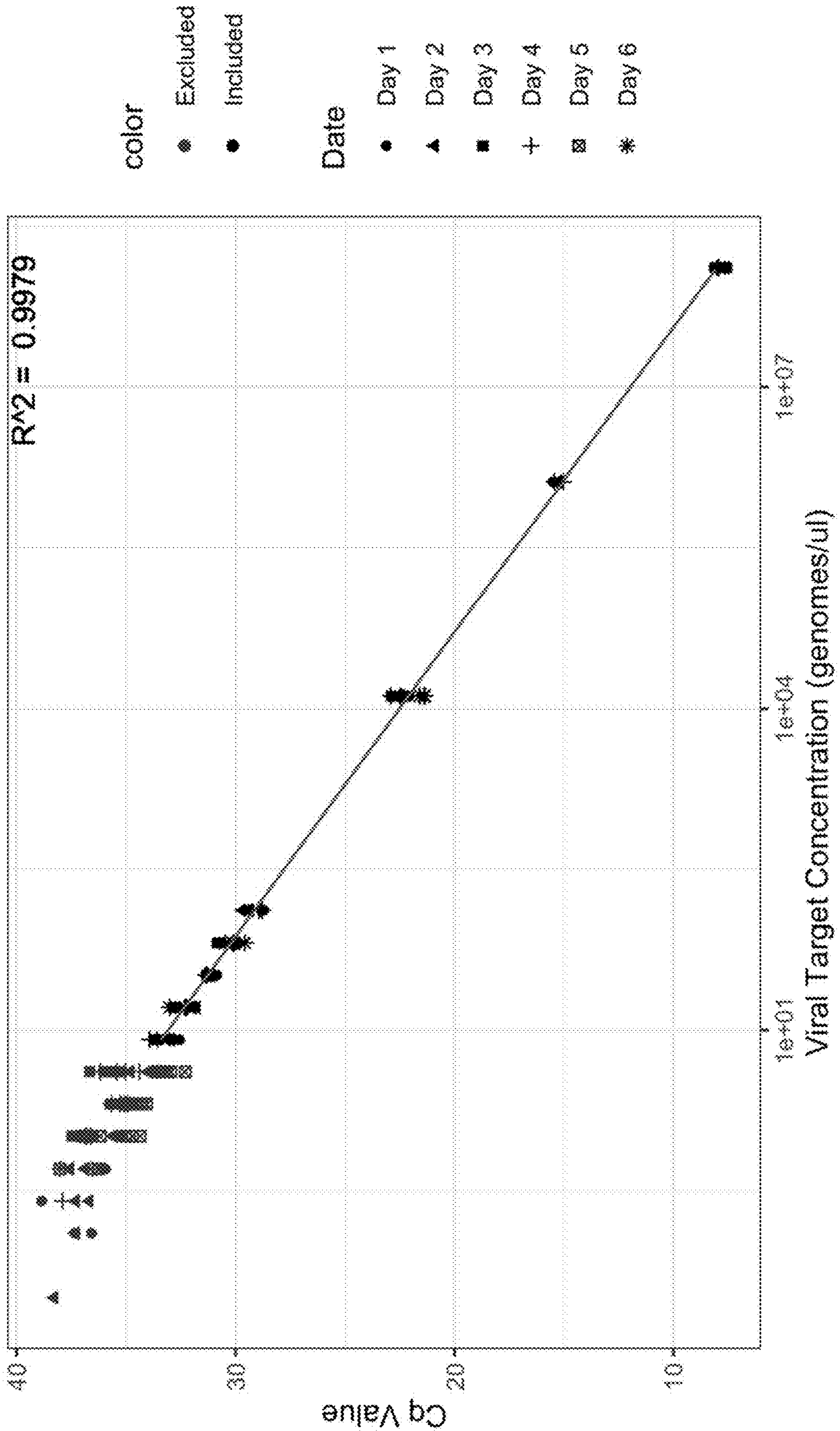
FIG. 4 illustrates the linear range of TG-N2 assay with extracted synthetic material across days.

In FIG. 4, linear range of TG-N2 assay with extracted synthetic material across days is presented. Points in the upper left of the plot indicate samples with concentrations below the LoQ, and the remaining points shown with the plot line indicate samples above the LoQ. FIG. 5 shows results of SARS-CoV-2 assay validation and linear range across all validation days (Mean, (SD, % CV) [n amplified/total]).

RNase P Validation

The RNase P assay was validated using human genomic DNA and the TGen North SARS-CoV-2 Quantitative RT-qPCR Protocol across several days. Using these data, the LoD and LoQ were determined. The LoD and LoQ was determined to be XX ng/ul. Based on a high amount of day to day variability, a model was fitted to consider day to day variation allowing a decrease in the LoQ, since this reduces the variability of the assay.

Figure 6:
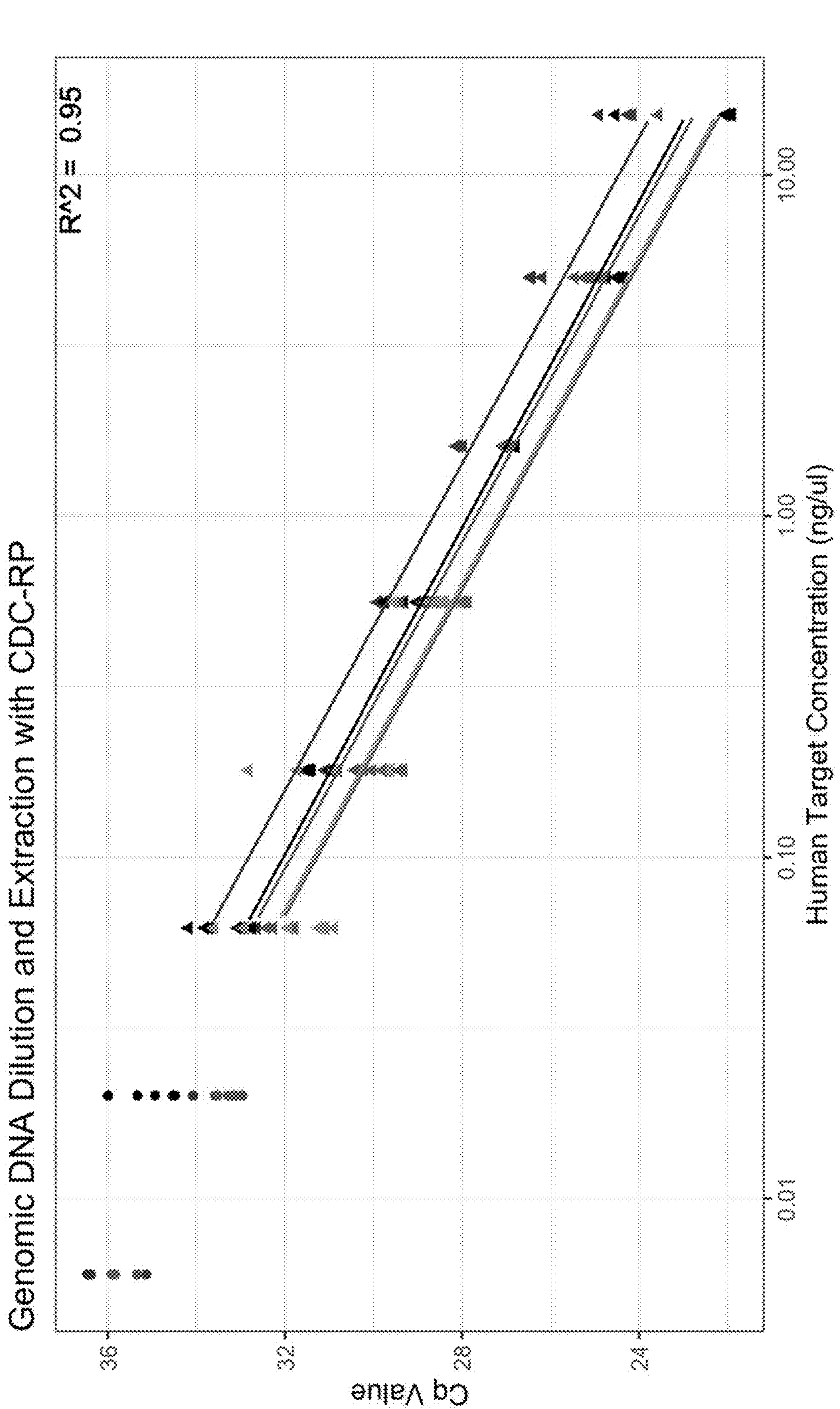
FIG. 6 illustrates linear range of RNase P assay with quantified human genomic DNA; lines indicate samples completed across different days, linear model with an offset was fit across the data to control for day-to-day variation.

FIG. 6 presents linear range of RNase P assay with quantified human genomic DNA. Different lines indicate samples completed across different days, linear model with an offset was fit across the data to control for day-to-day variation. FIG. 7 presents results of DNA RNase P assay validation and linear range across all validation days (Mean, (SD, % CV) [n amplified/total]).

It is to be understood that unless specifically stated otherwise, references to "a," "an," and/or "the" may include one or more than one and that reference to an item in the singular may also include the item in the plural. Reference to an element by the indefinite article "a," "an" and/or "the" does not exclude the possibility that more than one of the elements are present, unless the context clearly requires that there is one and only one of the elements.

As used herein, the term "comprise," and conjugations or any other variation thereof, are used in its non-limiting sense to mean that items following the word are included, but items not specifically mentioned are not excluded.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

REFERENCES

The publications discussed herein are provided solely for their disclosure prior to the filing date of the present application. Nothing herein is to be construed as an admission that the present invention is not entitled to antedate such publication by virtue of prior invention.

U.S. Food and Drug Administration. Emergency Use Authorization. https://www.fda.gov/emergency-preparedness-and-response/mcm-legal-regulatory-and-policy-framework/emergency-use-authorization (2021).

Beigel, J. H. et al. Remdesivir for the Treatment of Covid-19—Final Report. *N. Engl. J. Med.* 383, 1813-1826 (2020).

The RECOVERY Collaborative Group. Dexamethasone in Hospitalized Patients with Covid-19. *N. Engl. J. Med.* 384, 693-704 (2021).

Gottlieb, R. L. et al. Effect of Bamlanivimab as Monotherapy or in Combination with Etesevimab on Viral Load in Patients with Mild to Moderate COVID-19: A Randomized Clinical Trial. *JAMA—J. Am. Med. Assoc.* 46225, 1-13 (2021).

Shen, C. et al. Treatment of 5 Critically Ill Patients with COVID-19 with Convalescent Plasma. *JAMA—J. Am. Med. Assoc.* 323, 1582-1589 (2020).

Piubelli, C. et al. Overall decrease in SARS-CoV-2 viral load and reduction in clinical burden: the experience of a hospital in northern Italy. *Clin. Microbiol. Infect.* 27, 131.e1-131.e3 (2021).

Zhou, R. et al. Viral dynamics in asymptomatic patients with COVID-19. *Int. J. Infect. Dis.* 96, 288-290 (2020).

Han, M. S., Byun, J. H., Cho, Y. & Rim, J. H. RT-PCR for SARS-CoV-2: quantitative versus qualitative. *Lancet* Infect. Dis. 21, 165 (2021).

Dahdouh, E., Lázaro-Perona, F., Romero-Gómez, M. P., Mingorance, J. & García-Rodriguez, J. Ct values from SARS-CoV-2 diagnostic PCR assays should not be used as direct estimates of viral load. *J. Infect.* 2020-2022 (2020) doi:10.1016/j.jinf.2020.10.017.

Cao, B. et al. A trial of lopinavir-ritonavir in adults hospitalized with severe covid-19. *N. Engl. J. Med.* 382, 1787-1799 (2020).

Pan, Y., Zhang, D., Yang, P., Poon, L. L. M. & Wang, Q. Viral load of SARS-CoV-2 in clinical samples. *Lancet Infect. Dis.* 20, 411-412 (2020).

Caillard, S., Benotmane, I., Gautier Vargas, G., Perrin, P. & Fafi-Kremer, S. SARS-CoV-2 viral dynamics in immunocompromised patients. *Am. J. Transplant.* (2020) doi:10.1111/ajt.16353.

Liu, Y. et al. Viral dynamics in mild and severe cases of COVID-19. *Lancet Infect. Dis.* 20, 656-657 (2020).

Schmittgen, T. D. & Livak, K. J. Analyzing real-time PCR data by the comparative CT method. *Nat. Protoc.* 3, 1101-1108 (2008).

Jacob, F. et al. Careful Selection of Reference Genes Is Required for Reliable Performance of RT-qPCR in Human Normal and Cancer Cell Lines. *PLOS One* 8, (2013).
Kozera, B. & Rapacz, M. Reference genes in real-time PCR. *J. Appl. Genet.* 54, 391-406 (2013).

What is claimed is:

1. A method of detecting severe acute respiratory syndrome coronavirus 2 (SARS-CoV-2) in a subject, comprising:

separately isolating, purifying and concentrating RNA and DNA from a sample obtained from the subject;

performing a quantitative real-time reverse transcription-polymerase chain reaction (RT-qPCR) assay on the isolated RNA using:

(a) a first primer comprising SEQ ID NO:7, (b) a second primer comprising SEQ ID NO:12, and (c) a first probe comprising SEQ ID NO:8;

performing a quantitative real-time polymerase chain reaction (qPCR) assay on the isolated DNA using:

(d) a third primer comprising SEQ ID NO:9, (e) a fourth primer comprising SEQ ID NO:10, and (f) a second probe comprising SEQ ID NO:11;

wherein the first and second probe comprises a fluorescent dye and a quencher dye; and detecting the presence or absence of SARS-CoV-2 by analyzing the nucleic acid amplification products of the RT-qPCR assay and qPCR assay.

2. The method of claim 1, wherein the sample is a nasopharangeal sample.

3. The method of claim 2, wherein the nasopharangeal sample is placed in phosphate buffered saline (PBS), viral transport media (VTM) or universal transport medium (UTM).

4. The method of claim 1, wherein both SARS-Cov-2 RNA and human DNA in the sample are quantified and the SARS-Cov-2 viral load is normalized by comparison with human DNA load in the specimen.

5. The method of claim 1, wherein the sample comprises one or more of miRNA, tRNA, siRNA, mRNA, cDNA, genomic DNA sequences, single-stranded DNA, or complementary sequences thereof.

6. The method of claim 1, wherein detecting the presence or absence of SARS-CoV-2 comprises incorporation of fluorescent dye into the nucleic acid amplification products.

7. The method of claim 6, wherein the fluorescent signal is monitored with each cycle of PCR.

8. The method of claim 1, wherein the detecting the presence or absence of SARS-CoV-2 is quantitative.

* * * * *

SEQUENCE LISTING

```
Sequence total quantity: 12
SEQ ID NO: 1            moltype = DNA  length = 21
FEATURE                 Location/Qualifiers
source                  1..21
                        mol_type = genomic DNA
                        organism = Homo sapiens
SEQUENCE: 1
cccgcattac gtttggtgga c                                              21

SEQ ID NO: 2            moltype = DNA  length = 49
FEATURE                 Location/Qualifiers
source                  1..49
                        mol_type = genomic DNA
                        organism = Homo sapiens
SEQUENCE: 2
atagctaata cgactcacta tagggctctg cggtaaggct tgagtttca                49

SEQ ID NO: 3            moltype = DNA  length = 21
FEATURE                 Location/Qualifiers
source                  1..21
                        mol_type = genomic DNA
                        organism = Homo sapiens
SEQUENCE: 3
gtccttccct cagtcagcac c                                              21

SEQ ID NO: 4            moltype = DNA  length = 47
FEATURE                 Location/Qualifiers
source                  1..47
                        mol_type = genomic DNA
                        organism = Homo sapiens
SEQUENCE: 4
atagctaata cgactcacta taggggcact ggctcagagt cgtcttc                  47

SEQ ID NO: 5            moltype = DNA  length = 1272
FEATURE                 Location/Qualifiers
source                  1..1272
                        mol_type = genomic DNA
                        organism = Homo sapiens
SEQUENCE: 5
atgtctgata atggacccca aaatcagcga aatgcacccc gcattacgtt tggtggaccc  60
tcagattcaa ctggcagtaa ccagaatgga gaacgcagtg gggcgcgatc aaaacaacgt  120
cggccccaag gtttacccaa taatactgcg tcttggttca ccgctctcac tcaacatggc  180
aaggaagacc ttaaattccc tcgaggacaa ggcgttccaa ttaacaccaa tagcagtcca  240
gatgaccaaa ttggctacta ccgaagagct accagacgaa ttcgtggtgg tgacggtaaa  300
atgaaagatc tcagtccaag atggtatttc tactacctag gaactgggcc agaagctgga  360
cttccctatg gtgctaacaa agacggcatc atatgggttg caactgaggg agccttgaat  420
acaccaaaag atcacattgg cacccgcaat cctgctaaca atgctgcaat cgtgctacaa  480
cttcctcaag gaacaacatt gccaaaaggc ttctacgcag aagggagcag aggcggcagt  540
caagcctctt ctcgttcctc atcacgtagt cgcaacagtt caagaaattc agatcagatc  600
gcaactccag gcagcagtag gggaacttct cctgctagaa tggctggcaa tggcggtgat  660
gctgctcttg ctttgctgct gcttgacaga ttgaaccagc ttgagagcaa aatgtctggt  720
aaaggccaac aacaacaagg ccaaactgtc actaagaaat ctgctgctga ggcttctaag  780
aagcctcggc aaaaacgtac tgccactaaa gcatacaatg taacacaagc tttcggcaga  840
cgtggtccag aacaaaccca aggaaatttt ggggaccagg aactaatcag acaaggaact  900
gattacaaac attggccgca aattgcacaa tttgccccca gcgcttcagc gttcttcgga  960
atgtcgcgca ttggcatgga agtcacacct tcgggaacgt ggttgaccta cacaggtgcc  1020
atcaaattgg atgacaaaga tccaaatttc aaagatcaag tcattttgct gaataagcat  1080
attgacgcat acaaaacatt cccaccaaca gagcctaaaa aggacaaaaa gaagaaggct  1140
gatgaaactc aagccttacc gcagagacag aagaaacagc aaactgtgac tcttcttcct  1200
gctgcagatt tggatgattt ctccaaacaa ttgcaacaat ccatgagcag tgctgactca  1260
actcaggcct aa                                                        1272

SEQ ID NO: 6            moltype = DNA  length = 673
FEATURE                 Location/Qualifiers
source                  1..673
                        mol_type = genomic DNA
                        organism = Homo sapiens
```

-continued

```
SEQUENCE: 6
gtccttccct cagtcagcac ctcatggtgt agtcttcttg catgtgactt atgtccctgc  60
acaagaaccc cacttcacaa ctgctcctgc catttgtcat gatggaaaag cacactttcc  120
tcgtgaaggt gtctttgttt caaatggcac acactggttt gtaacacaaa ggaattttta  180
tgaaccacaa atcattacta cagacaacac atttgtgtct ggtaactgtg atgttgtaat  240
aggaattgtc aacaacacag tttatgatcc tttgcaacct gaattagact cattcaagga  300
ggagttagat aaatatttta agaatcatac atcaccagat gttgatttag gtgacatctc  360
tggcattaat gcttcagttg taaacattca aaaagaaatt gaccgcctca atgaggttgc  420
caagaattta aatgaatctc tcatcgatct ccaagaactt ggaaagtatg agcagtatat  480
aaaatggcca tggtacattt ggctaggttt tatagctggc ttgattgcca tagtaatggt  540
gacaattatg ctttgctgta tgaccagttg ctgtagttgt ctcaagggct gttgttcttg  600
tggatcctgc tgcccccttg atgaagacga ctctgagcca gtgctcaaag gagtcaaatt  660
acattacaca taa                                                    673

SEQ ID NO: 7            moltype = DNA  length = 21
FEATURE                 Location/Qualifiers
source                  1..21
                        mol_type = genomic DNA
                        organism = Homo sapiens
SEQUENCE: 7
ttcagcgttc ttcggaatgt c                                           21

SEQ ID NO: 8            moltype = DNA  length = 23
FEATURE                 Location/Qualifiers
source                  1..23
                        mol_type = genomic DNA
                        organism = Homo sapiens
SEQUENCE: 8
cgcattggca tggaagtcac acc                                         23

SEQ ID NO: 9            moltype = DNA  length = 19
FEATURE                 Location/Qualifiers
source                  1..19
                        mol_type = genomic DNA
                        organism = Homo sapiens
SEQUENCE: 9
agatttggac ctgcgagcg                                              19

SEQ ID NO: 10           moltype = DNA  length = 20
FEATURE                 Location/Qualifiers
source                  1..20
                        mol_type = genomic DNA
                        organism = Homo sapiens
SEQUENCE: 10
gagcggctgt ctccacaagt                                             20

SEQ ID NO: 11           moltype = DNA  length = 23
FEATURE                 Location/Qualifiers
source                  1..23
                        mol_type = genomic DNA
                        organism = Homo sapiens
SEQUENCE: 11
ttctgacctg aaggctctgc gcg                                         23

SEQ ID NO: 12           moltype = DNA  length = 20
FEATURE                 Location/Qualifiers
source                  1..20
                        mol_type = genomic DNA
                        organism = Homo sapiens
SEQUENCE: 12
tggcacctgt gtaggtcaac                                             20
```